United States Patent
Dinca et al.

(10) Patent No.: US 9,758,532 B2
(45) Date of Patent: Sep. 12, 2017

(54) COMPOSITIONS AND METHODS COMPRISING POROUS METAL ORGANIC FRAMEWORKS AND RELATED USES

(71) Applicant: Massachusetts Institute of Technology, Cambridge, MA (US)

(72) Inventors: Mircea Dinca, Somerville, MA (US); Casey R. Wade, Waltham, MA (US)

(73) Assignee: Massacusetts Institute of Technology, Cambridge, MA (US)

( * ) Notice: Subject to any disclaimer, the term of this patent is extended or adjusted under 35 U.S.C. 154(b) by 292 days.

(21) Appl. No.: 14/270,385

(22) Filed: May 6, 2014

(65) Prior Publication Data

US 2014/0326007 A1 Nov. 6, 2014

Related U.S. Application Data

(60) Provisional application No. 61/819,716, filed on May 6, 2013.

(51) Int. Cl.
*C07F 3/06* (2006.01)

(52) U.S. Cl.
CPC .................................. *C07F 3/06* (2013.01)

(58) Field of Classification Search
CPC ....................................................... C07F 3/06
See application file for complete search history.

(56) References Cited

U.S. PATENT DOCUMENTS

2012/0077667 A1* 3/2012 Liu .................... H01M 4/8605
502/101

OTHER PUBLICATIONS

International Search Report and Written Opinion for PCT/US2014/036885 mailed Sep. 5, 2014.
Henninger et al., MOFs for Use in Adsorption Heat Pump Processes. European Journal of Inorganic Chemistry. Jun. 2012; 2012(16): 2625-34.
Akiyama et al., Effect of functional groups in MIL-101 on water sorption behavior. Microporous and Mesoporous Materials. 2012;157:89-93.
Bonaccorsi et al., Hydrothermal and microwave synthesis of SAPO (CHA) zeolites on aluminium foams for heat pumping applications. Microporous and Mesoporous Mater. 2013;167:30-37.
Caskey et al., Dramatic tuning of carbon dioxide uptake via metal substitution in a coordination polymer with cylindrical pores. J Am Chem Soc. Aug. 20, 2008;130(33):10870-1. doi: 10.1021/ja8036096. Epub Jul. 29, 2008.
Choi et al., Broadly hysteretic H2 adsorption in the microporous metal-organic framework Co(1,4-benzenedipyrazolate). J Am Chem Soc. Jun. 25, 2008;130(25):7848-50. doi: 10.1021/ja8024092. Epub May 31, 2008.
Choi et al., Hydrogen storage in water-stable metal-organic frameworks incorporating 1,3 and 1,4 benzenedipyrazolate. Energy Environ Sci. 2010;3:117-23.
Cychosz et al., Water stability of microporous coordination polymers and the adsorption of pharmaceuticals from water. Langmuir. Nov. 16, 2010;26(22):17198-202. doi: 10.1021/la103234u. Epub Oct. 5, 2010.
Ehrenmann et al., Water adsorption characteristics on MIL-101 for heat-transformation application of MOFs. Eur J Inorg Chem. 2011;2011(4):471-474.
Furukawa et al., Water adsorption in porous metal-organic frameworks and related materials. J Am Chem Soc. Mar. 19, 2014;136(11):4369-81. doi: 10.1021/ja500330a. Epub Mar. 11, 2014.
Gargiulo et al., Synthesis and characterization of a microporous copper triazolate as a water vapor adsorbent. Microporous and Mesoporous Mater. 2011;145:74-9.
Henninger et al., MOFs as adsorbents for low temperature heating and cooling applications. J Am Chem Soc. Mar. 4, 2009;131(8):2776-7. doi: 10.1021/ja808444z.
Henninger et al., MOFs for Use in Adsorption Heat Pump Processes. Eur. J. Inorg. Chem. 2012;2012:2625-34.
Henninger et al., Novel sorption materials for solar heating and cooling. Energy Procedia. 2012;30:279-88.
Henninger et al., Water adsorption characteristics of novel materials for heat transformation applications. Appl. Therm. Eng. 2010;30:1692-1702.
Henninger et al., Characterisation and improvement of sorption materials with molecular modeling for the use of heat transformation applications. Adsorption. 2011;17:833-43.
Janchen et al., Studies of the water adsorption on Zeolites and modified mesoporous materials for seasonal storage of solar heat. Solar Energy. 2004;76:339-44.
Jeremias et al., Programming MOFs for water sorption: aminofunctionalized MIL-125 and UiO-66 for heat transformation and heat storage applications. Dalton Trans. Dec. 7, 2013;42(45):15967-73. doi: 10.1039/c3dt51471d. Epub Jul. 18, 2013.
Jeremias et al., Water and methanol adsorption on MOFs for cycling heat transformation processes. New J Chem. 2014;38:1846-52.
Jeremias et al., MIL-100(Al, Fe) as water adsorbents for heat transformation purposes—a promising application. J Mater Chem. 2012;22:10148-10151.
Khutia et al., Water sorption cycle measurements on functionalized MIL-101 Cr for heat transformation application. Chem Mater. 2013;25:790-798.
Kusgens et al., Characterization of metal-organic frameworks by water adsorption. Microporous and Mesoporous Mater. 2009;120:325-330.
Low et al., Virtual high throughput screening confirmed experimentally: porous coordination polymer hydration. J. Am. Chem. Soc. Nov. 4, 2009;131(43):15834-42. doi: 10.1021/ja9061344.
Makal et al., Methane storage in advanced porous materials. Chem Soc Rev. Dec. 7, 2012;41(23):7761-79. doi: 10.1039/c2cs35251f.
Ng et al., Experimental investigation of the silica gel-water adsorption isotherm characteristics. Appl. Therm Eng. 2001;21:1631-42.

(Continued)

*Primary Examiner* — Joseph Kosack
(74) *Attorney, Agent, or Firm* — Wolf, Greenfield & Sacks, P.C.

(57) ABSTRACT

Compositions and methods comprising metal organic frameworks (MOFs) and related uses are generally provided. In some embodiments, an MOF comprises a plurality of metal ions, each coordinated with at least one ligand comprising at least two unsaturated N-heterocyclic aromatic groups arranged about an organic core. In some embodiments, an MOF may be used in applications related to water adsorption.

25 Claims, 8 Drawing Sheets

(56) References Cited

OTHER PUBLICATIONS

Ristic et al., The performance of small-pore microporous aluminophosphates in low-temperature solar energy storage: the structure-property relationship. Adv Func Mater. 2012;22:1952-7.

Schoenecker et al., Effect of water adsorption on retention of structure and surface area of metal-organic frameworks. Ind Eng Chem Res. 2012;51:6513-6519.

Suh et al., Hydrogen storage in metal-organic frameworks. Chem Rev. 2012;112:782-835.

Sumida et al., Carbon dioxide capture in metal-organic frameworks. Chem Rev. Feb. 8, 2012;112(2):724-81. doi: 10.1021/cr2003272. Epub Dec. 28, 2011.

Tatsidjodoung et al., A review of potential materials for thermal energy storage in building applications. Renew. Sust. Energ. Rev. 2013;18:327-49.

Tonigold et al., Pyrazolate-based cobalt(II)-containing metal-organic frameworks in heterogeneous catalytic oxidation reactions: elucidating the role of entatic states for biomimetic oxidation processes. Chemistry. Jul. 25, 2011;17(31):8671-95. doi: 10.1002/chem.201003173. Epub Jun. 17, 2011.

Wade, Designing functionality for anion detection with molecular receptors and small molecule adsorption in microporous materials. PowerPoint Presentation. Brandeis University. Dec. 4, 2012.

Wade et al., Investigation of the synthesis, activation, and isosteric heats of $CO_2$ adsorption of the isostructural series of metal-organic frameworks $M_3(BTC)_2$ (M = Cr, Fe, Ni, Cu, Mo, Ru). Dalton Trans. Jul. 14, 2012;41(26):7931-8. doi: 10.1039/c2dt30372h. Epub Apr. 26, 2012.

Wade et al., Postsynthetic tuning of hydrophilicity in pyrazolate MOFs to modulate water adsorption properties. Energy Environ. Sci. 2013;6:2172-7.

Wickenheisser et al., Grafting of hydrophilic ethylene glycols or ethylenediamine on coordinatively unsaturated metal sites in MIL-100(Cr) for improved water adsorption characteristics. Inorganica Chimica Acta. 2013;407:145-52.

Wu et al., Adsorption sites and binding nature of $CO_2$ in prototypical metal-organic frameworks: a combined neutron diffraction and first-principles study. J Phys Chem Lett. 2010;1(13):1946-51.

\* cited by examiner

COMPOSITIONS AND METHODS COMPRISING POROUS METAL ORGANIC FRAMEWORKS AND RELATED USES

RELATED APPLICATIONS

This application claims priority under 35 U.S.C. §119(e) to U.S. Provisional Application No. 61/819,716, filed May 6, 2013, entitled "Metal-Organic Frameworks with Tunable Hydrophilicity For Water Adsorption Applications".

FIELD

Compositions and methods comprising metal organic frameworks (MOFs) and related uses are generally provided. In some embodiments, a MOF comprises a plurality of metal ions, each coordinated with at least one ligand comprising at least two unsaturated N-heterocyclic aromatic groups arranged about an organic core.

BACKGROUND

Porous materials such as silicas and zeolites have been examined as adsorbents in water-based adsorption heat pumps and heat storage devices. Silicas generally display poor water exchange capacities, in part due to low hydrophilicity. Water exchange capacity, the amount of water adsorbed and desorbed per gram adsorbent during the working and regeneration cycles, is an important feature since it relates to the amount of heat transferred in a given cycle. More hydrophilic zeolites and zeolite-type materials have been shown to exhibit increased water exchange capacities, as compared to silicas but the increase in hydrophilicity leads to higher desorption temperatures which may surpass those provided by low-temperature waste heat or solar collectors.

While much effort has been placed toward tuning the structure and function of metal organic frameworks (MOFs) for adsorption and separation of gases such as $H_2$, $CH_4$, and $CO_2$, less attention has been given toward modifying their water adsorption properties. This is due, at least in part, to the hydrolytic instability of many MOFs. The water adsorption behaviors of the few water-stable MOFs containing carboxylate-based ligands have been studied in some detail and evidenced characteristics desirable in heat pump adsorbents. While some metal-organic frameworks in general have attracted interest as adsorbents in water-based adsorption heat pumps, many have low water loading capacities.

Accordingly, improved compositions and methods are needed.

SUMMARY

In some embodiments, a metal organic framework (MOF) is provided comprising a plurality of metal ions, each coordinated with at least one ligand, wherein each ligand comprises at least two unsaturated N-heterocyclic aromatic groups arranged about an organic core, wherein the unsaturated N-heterocyclic aromatic groups are selected from the group consisting of pyrazolate, imidazolate, and tetrazolate. In some embodiments, the MOF is used for water absorption.

In some embodiments, methods are provided comprising using an MOF for water adsorption, wherein the MOF comprising a plurality of metal ions, each coordinated with at least one ligand, wherein each ligand comprises at least two unsaturated N-heterocyclic aromatic groups arranged about a core. In some embodiments, the at least two unsaturated N-heterocyclic aromatic groups are selected from the group consisting of pyrazolate, pyrrolate, imidazolate, triazolate, and tetrazolate.

Figure 1:
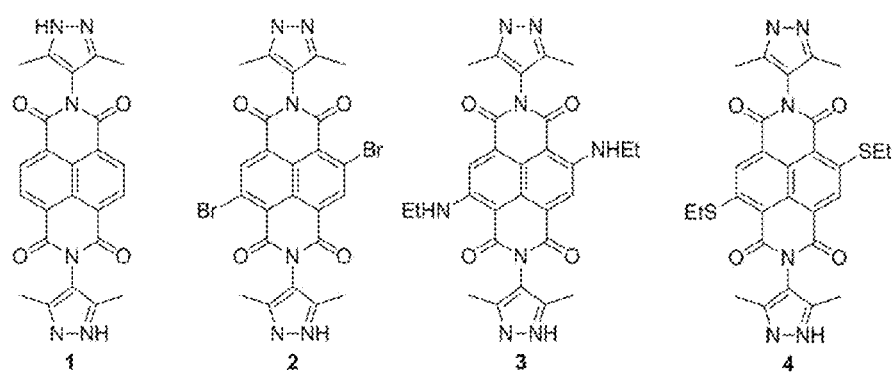
FIG. 1 shows non-limiting examples of ligands, for use in MOFs according to some embodiments.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Compositions and methods comprising metal organic frameworks (MOFs) and related uses are generally provided. In some embodiments, an MOF comprises a plurality of metal ions, each coordinated with at least one ligand, wherein each ligand comprises at least two unsaturated N-heterocyclic aromatic groups arranged about an organic core.

The term "metal-organic framework" is given its ordinary meaning in the art and refers to a one-, two-, or three-dimensional coordination polymer including metal ions and ligands which function as organic structural units, wherein a portion of the metal ions are each chemically bonded to at least one bi-, tri- or poly-dentate organic structural unit. The metal ions, in addition to being coordinated with at least one ligand, may also be bound to one or more auxiliary ligands, as described in more detail herein.

In some embodiments, an MOF comprises a plurality of metal ions, each coordinated with at least one ligand comprising at least two unsaturated N-heterocyclic aromatic groups arranged about an organic core. In some embodiments, a portion of the metal ions are associated with two, three, or four ligands, and each of those ligand is individually associated with one, two, three, or four metal ions. In some embodiments, a portion of the metal ions are associated with two ligands, and each of those ligand is individually associated with two metal ions. In some embodiments, a portion of the metal ions are associated with three ligands, and each of those ligand is individually associated with three metal ions. In some embodiments, a portion of the metal ions are associated with four ligands, and each of those ligand is individually associated with two metal ions.

In some embodiments, each ligand comprises two unsaturated N-heterocyclic aromatic groups. In some embodiments, each ligand comprises three unsaturated N-heterocyclic aromatic groups. In some embodiments, each ligand comprises four unsaturated N-heterocyclic aromatic groups.

The unsaturated N-heterocyclic aromatic group may be selected from any suitable group. Non-limiting examples of are pyrrolate, pyrazolate, triazolate, imidazolate, and tetrazolate. In some embodiments, the unsaturated N-heterocyclic aromatic groups are selected from the group consisting of pyrazolate, triazolate, imidazolate, and tetrazolate. In some embodiments, the unsaturated N-heterocyclic aromatic groups are selected from the group consisting of pyrazolate, imidazolate, and tetrazolate. In some embodiments, the unsaturated N-heterocyclic aromatic groups are pyrazolates. Non-limiting examples of triazolate include 1,2,4-triazolate and 1,2,3-triazolate. In some embodiments, the ligand comprises two pyrazolate groups. In some embodiments, a ligand is charged. In some embodiments, a ligand has a charge of (−1), or (−2), or (−3), or (−4). In some embodiments, a ligand has a charge of (−2).

The organic core of the ligand comprising at least two unsaturated N-heterocyclic aromatic groups may be any suitable core. In some embodiments, the core is aromatic. Generally, the core comprises a rigid structure formed from fused aryl and/or heteroaryl rings. In some embodiments, the organic core comprises a plurality of fused aryl and/or heteroaryl rings. In some cases, the organic core comprises a plurality of fused aryl rings. In some cases, the organic core comprises one or more of benzyl, thiophenyl, carbazolyl, pyrrolyl, indolyl, and furanyl.

In some embodiments, each ligand has the structure [Q-(Ar)$_m$]$^{m-}$, wherein each Ar is the same or different and is an unsaturated N-heterocyclic aromatic group, Q is an organic core, and m is 2, 3, or 4. In some embodiments, each Ar is the same or different and is selected from the group consisting of pyrazolate, pyrrolate, triazolate, imidazolate, and tetrazolate. In some embodiments, each Ar is the same or different and is selected from the group consisting of pyrazolate, triazolate, imidazolate, and tetrazolate. In some embodiments, each Ar is the same or different and is selected from the group consisting of pyrazolate, imidazolate, and tetrazolate. In some embodiments, each Ar is pyrazolate. In some embodiments, each m is 2. In some embodiments, each m is 3. In some embodiments, each m is 4. In some embodiments, Q comprises a plurality of fused aryl and/or heteroaryl rings. In some embodiments, m is 2 and Q comprises the structure:

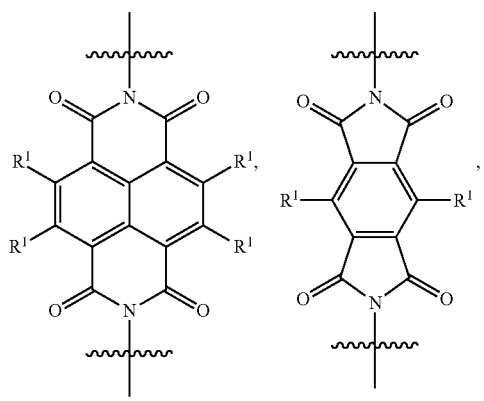

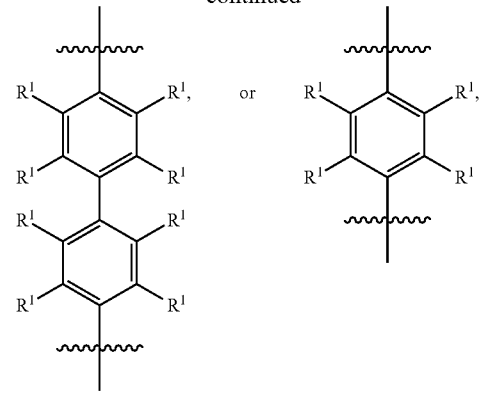

-continued wherein each R$^1$ is the same or different and is selected from the group consisting of hydrogen, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$, wherein each R' is the same or different and is optionally substituted alkyl or optionally substituted aryl.

In some embodiments, Q is:

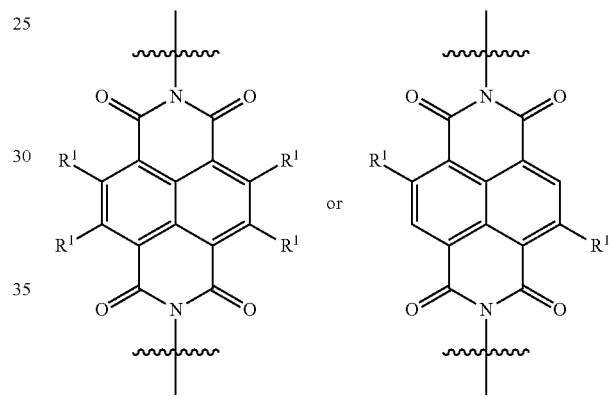

wherein each R$^1$ is the same or different and is selected from the group consisting of hydrogen, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', —NHR', and —NH$_2$, wherein each R' is the same or different and is optionally substituted alkyl or optionally substituted aryl.

In some embodiments, Q is:

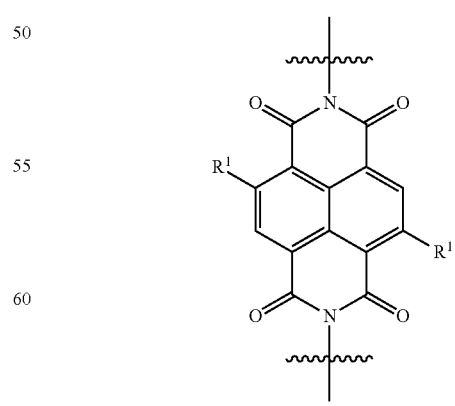

and each R$^1$ is hydrogen, halide (e.g., Br), NHR', or SR', wherein each R' is the same or different and is optionally substituted alkyl or optionally substituted aryl. In some embodiments, each $R^1$ is hydrogen, Br, NHEt, or SEt.

In some embodiments, the ligand comprises the structure:

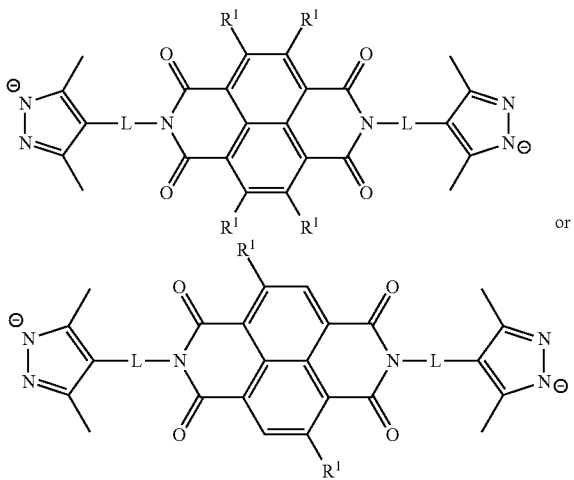

or wherein each $R^1$ is the same or different and is selected from the group consisting of hydrogen, —$NO_2$, —R', —F, —Cl, —Br, —I, —CN, —NC, —$SO_3R'$, —$SO_3H$, —OR', —OH, —SR', —SH, —$PO_3R'$, —$PO_3H$, —$CF_3$, —$NR'_2$, —NHR', and —$NH_2$; each L is the same or different and is absent or selected from the group consisting of optionally substituted alkylene, optionally substituted heteroalkylene, optionally substituted arylene, and optionally substituted heteroarylene; and each R' is the same or different and is optionally substituted alkyl or optionally substituted aryl. In some embodiments, each L is the same or different and is selected from the group consisting of optionally substituted alkylene, optionally substituted heteroalkylene, optionally substituted arylene, and optionally substituted heteroarylene.

In some embodiments, the ligand comprises the structure:

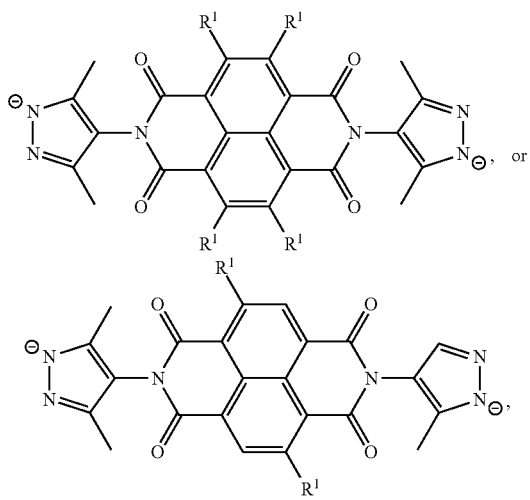

wherein each $R^1$ is the same or different and is selected from the group consisting of hydrogen, —$NO_2$, —R', —F, —Cl, —Br, —I, —CN, —NC, —$SO_3R'$, —$SO_3H$, —OR', —OH, —SR', —SH, —$PO_3R'$, —$PO_3H$, —$CF_3$, —$NR'_2$, —NHR', and —$NH_2$, wherein each R' is the same or different and is optionally substituted alkyl or optionally substituted aryl. In some embodiments, each $R^1$ is hydrogen, halide (e.g., Br), NHR', or SR', wherein each R' is the same or different and is optionally substituted alkyl or optionally substituted aryl. In some embodiments, each $R^1$ is hydrogen, Br, NHEt, or SEt.

In some embodiments, more than one type of ligand may be employed, for example, a first type of ligand and a second type of ligand. The two or more types of ligands may be provided in any suitable ratio. In some embodiments, following synthetic modification of an MOF or a precursor ligand which is to be utilized to form an MOF, a mixture of types of ligands (or precursor ligands) may be present. For example, the ligands within the MOF or a plurality of precursor ligands that will be used to from an MOF may be synthetically modified (e.g., oxidized) and only a portion of the substituents of the ligands or precursor ligands may be altered. Thus, the ligands within the MOF or the precursor ligands used to form the MOF may comprise a number of different substitution patterns. As a non-limiting example, if the ligand (or precursor ligand) comprises two substituents that are targeted to be modified, upon modification of a plurality of the ligands, for each ligand within the plurality, both substituents may be modified, or only one substituent may be modified, or neither substituent may be modified. Thus, the plurality of ligands may comprise some ligands with both substituents modified, some ligands with only one substituent modified, and some ligands with neither substituent modified.

Any suitable metal ion may be employed. Each metal ion may be monovalent, divalent, or trivalent. In some embodiments, each metal ion is a monovalent metal ion. Non-limiting examples of monovalent metal ions are $Ag^+$, $Cu^+$, and $Au^+$. In some embodiments, the metal ion is a divalent metal ion. Non-limiting examples of monovalent metal ions are $Mg^{2+}$, $Mn^{2+}$, $Fe^{2+}$, $Co^{2+}$, $Ni^{2+}$, $Cu^{2+}$, $Pd^{2+}$, $Pt^{2+}$, $Ru^{2+}$, $Cd^{2+}$, $zn^{2+}$, $Pb^{2+}$, $Hg^{2+}$, $V^{2+}$, $Cr^{2+}$, and $Ni^{+2}$. In some cases, the metal ion is Zn. In some embodiments, the metal ion is a trivalent metal ion. Non-limiting examples of trivalent metal ions are $Fe^{3+}$, $V^{3+}$, $Ti^{3+}$, $Sc^{3+}$, $Al^{3+}$, $In^{3+}$, $Ga^{3+}$, $Mn^{3+}$, $Co^{3+}$, and $Cr^{3+}$.

In some embodiments, more than one type of metal ion may be employed, for example, a first type of metal ion and a second type of metal ion. In some cases, the first type of metal ion and the second type of metal ion have the same valency. For example, the first type of metal ion may be a first type of divalent metal ion and the second type of metal ion may be a second different type of divalent metal ion. The two or more types of metal ions may be provided in any suitable ratio.

In some embodiments, a metal ion may be associated with one or more one auxiliary ligands. In some cases, the one or more auxiliary ligand may be found above and/or below the metal ion (e.g., as apical ligands). An auxiliary ligand may or might not be charged. Non-limiting examples of auxiliary ligands include halides (e.g., chlorine, fluorine, bromine, iodine), other salts (e.g., nitrate, carbonate, sulfonate, etc.), and coordinating solvents (e.g., water, pyridine, tetrahydrofuran, diethyl ether, etc.).

In some embodiments, methods of synthesis are provided. In some cases, a method of synthesizing an MOF comprises exposing a plurality of metal ions to a plurality of precursor ligands to form an MOF comprising a portion of the plurality of metal ions each coordinated with at least one ligand, wherein each ligand comprises at least two unsaturated N-heterocyclic aromatic groups arranged about an organic core. Non-limiting examples of ligands comprises at least unsaturated N-heterocyclic aromatic groups arranged about an organic core are described herein. In some embodiments, the metal ion is provided as a salt, and the at least one precursor ligand comprises at least two N-heterocyclic aromatic groups which, during the course of the reaction are oxidized to form the corresponding ligand (e.g., comprising unsaturated N-heterocyclic aromatic groups). For example, the precursor ligand may be oxidized to have a charge of (−1), or (−2), or (−3), or (−4).

In some embodiments, each precursor ligand comprises two N-heterocyclic aromatic groups. In some embodiments, each precursor ligand comprises three N-heterocyclic aromatic groups. In some embodiments, each precursor ligand comprises four N-heterocyclic aromatic groups. The N-heterocyclic aromatic group for the precursor ligand may be selected from any suitable group. Non-limiting examples are pyrrole, pyrazole, triazole, imadazole, and tetrazole. In some embodiments, the N-heterocyclic aromatic groups are selected from the group consisting of pyrazole, triazole, imidazole, and tetrazole. In some embodiments, the N-heterocyclic aromatic groups are selected from the group consisting of pyrazole, imidazole, and tetrazole. In some embodiments, the N-heterocyclic aromatic groups are pyrazoles. The organic core of the precursor ligand comprising at least two N-heterocyclic aromatic groups may be as described here.

In some embodiments, each precursor ligand has the structure Q-(Ar)$_m$, wherein each Ar is the same or different and is an N-heterocyclic aromatic group, Q is an organic core, and m is 2, 3, or 4. In some cases, Q and m are as described above for a ligand.

In some embodiments, the precursor ligand comprises the structure:

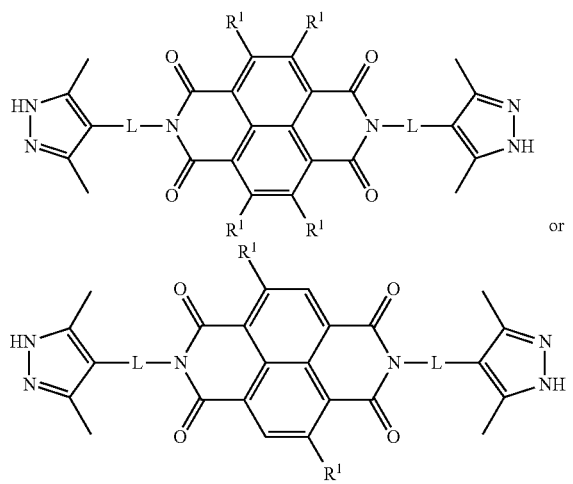

wherein each $R^1$ is the same or different and is selected from the group consisting of hydrogen, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$; each L is the same or different and is absent or selected from the group consisting of optionally substituted alkylene, optionally substituted heteroalkylene, optionally substituted arylene, and optionally substituted heteroarylene; and each R' is the same or different and is optionally substituted alkyl or optionally substituted aryl. In some embodiments, each L is the same or different and is selected from the group consisting of optionally substituted alkylene, optionally substituted heteroalkylene, optionally substituted arylene, and optionally substituted heteroarylene.

In some embodiments, the precursor ligand comprises the structure:

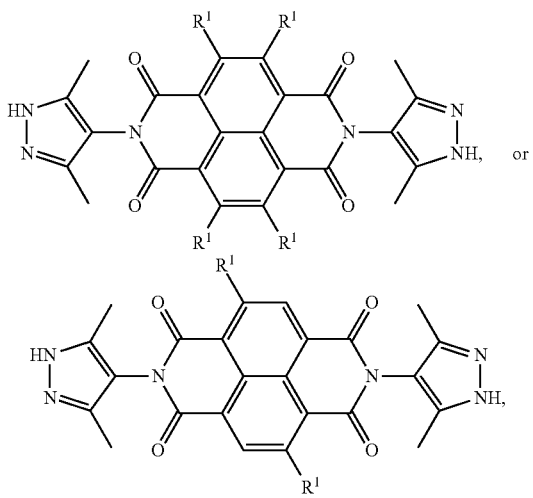

wherein each $R^1$ is the same or different and is selected from the group consisting of hydrogen, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$, wherein each R' is the same or different and is optionally substituted alkyl or optionally substituted aryl. In some embodiments, each $R^1$ is hydrogen, halide (e.g., Br), NHR', or SR', wherein each R' is the same or different and is optionally substituted alkyl or optionally substituted aryl. In some embodiments, each $R^1$ is hydrogen, Br, NHEt, or SEt.

The metal ion and the ligand may be provided in any suitable amounts. In some embodiments, the mole ratio of the metal ion to the ligand may be based upon the coordination of the metal ion to the ligand. For example, in embodiments, where the ligand is coordinated with three metal ions, and each metal ion is associated with two ligands, the mole ratio of the metal ion to the ligand may be at least 3:2. In some embodiments, the ligand is providing in slight mole excess.

In some embodiments, the metal ions are provided as a salt. Non-limiting examples of salts chloride, fluoride, bromide, iodide, NO$_3^-$, SO$_4^{2-}$, and ClO$_4^-$ salts.

Any suitable solvent may be utilized in the synthetic methods described herein. Non-limiting examples of solvents include water, methanol, ethanol, propanol, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide (DMSO), dimethylformamide, hexamethyl-phosphoric triamide, ethyl acetate, pyridine, triethylamine, picoline, mixtures thereof, or the like.

The methods of synthesis described herein may be carried out at any suitable temperature. In some cases, the reaction is carried out at about room temperature (e.g., about 25° C., about 20° C., between about 20° C. and about 25° C., or the like). In some cases, however, the reaction is carried out at temperatures below or above room temperature. In some embodiments, the reaction is carried at a temperature between about 25° C. and about 200° C., about 25° C. and about 150° C., or between about 50° C. and about 200° C., or between about 50° C. and about 150° C., or between about 100° C. and about 150° C.

In some embodiments, the methods of synthesis may be carried out in the presence of a base (e.g., to aid in deprotonation of the ligand). Non-limiting examples of bases include NR"$_3$ wherein each R" is the same or different and is hydrogen, optionally substituted alkyl, or optionally substituted aryl, and QOH, wherein Q is a cation (e.g., a metal cation, a semi-metal cation, $NH_4$).

In some embodiments, the synthetic methods may be carried out in an inert atmosphere. For example, the reactions may be carried out in or under an inert nitrogen or argon atmosphere (e.g., using standard Schlenk techniques and/or in an inert-atmosphere glovebox).

MOFs synthesized using the methods described herein may be purified using techniques known to those of ordinary skill in the art. In some embodiments, a synthesized MOF may be washed, sometimes involving a Soxhlet extractor, boiled, and/or sonicated (e.g., to remove excess starting materials).

In some embodiments, following synthesis of the MOF, the MOF may be modified. For example, the ligands of the MOF may be modified to include one or more functional groups and/or the one or more of the functional groups of the ligand may be modified. The ability to modify in the MOF following synthesis of the MOF is beneficial as the properties of the MOFs may be more readily tuned. For example, the MOF may be modified to incorporate hydrophobic or hydrophilic groups, which may decrease or increase, respectively, the water absorption abilities of the MOF. In some embodiments, the MOF is modified to include hydrophilic groups. The MOF may be modified using any suitable technique. In some embodiments, the MOF is exposed to oxidative conditions to associate new functional groups and/or modify currently present functional groups which are present on the ligand of the MOF. As a non-limiting example, a ligand of the MOF may comprise one or more alkyl sulfide groups, and the MOF may be exposed to oxidizing conditions (e.g., dimethyldioxirane) to modify the alkyl sulfide groups into alkyl sulfoxides or alkyl ethyl sulfones groups.

The MOFs, in some cases, may be formed as a film on a surface of a material. The film may be formed using techniques known to those of ordinary skill in the art. For example, the film may be formed by spin-casting method, drop-casting method, dip coating method, roll coating method, screen coating method, a spray coating method, screen printing method, ink-jet method, and the like. In some cases, the thickness of the film may be less than about 100 um (micrometer), less than about 10 um, less than about 1 um, less than about 100 nm, less than about 10 nm, less than about 1 nm, or thinner. In some cases, the film may have a thickness greater than 1 mm. In some embodiments, the substrate on which the film is formed may be a conductive. For example, the substrate may comprise quartz, indium-tin-oxide coated glass, silicon wafer, etc.

In some embodiments, the MOFs formed (e.g., a film of an MOF) may comprise little or no excess metal ions. That is, the MOF comprises essentially no metal ions which are not coordinated with a ligand comprising at least two unsaturated N-heterocyclic aromatic groups (i.e., "free metal ions"). In some embodiments, the MOF comprises less than about 0.5 wt %, or less then about 0.4 wt %, or less then about 0.3 wt %, or less than about 0.2 wt %, or less then about 0.1 wt %, or less than about 0.05 wt %, or less than about 0.03 wt %, or less than about 0.02 wt %, or less than about 0.01 wt %, or less than about 0.005 wt %, or less than about 0.001 wt % of free metal ions. Those of ordinary skill in the art will be aware of methods for determining the amount of free metal ions, for example, using XPS (e.g., see Example 1).

Figure 4:
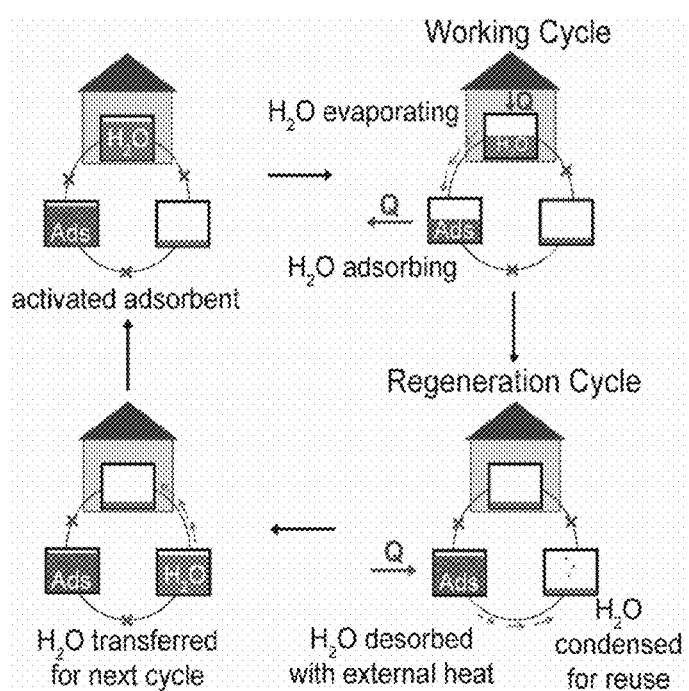
FIG. 4 shows a diagram of an intermittent adsorption cooling process, according to some embodiments.

The MOFs described herein or the MOFs synthesized using the methods described herein may be utilized in a wide variety of applications. In some embodiments, the MOFs may be utilized for water absorption. That is, the MOFs may be used in applications wherein water is to be absorbed. Such processes may find use, for example, in water-based absorption heat pumps. As will be known to those of ordinary skill in the art, a heat pump may operate according to the general cycle as shown in FIG. 4. In the working cycle, evaporation of a fluid, such as water, produces desired cooling in the application environment while adsorption of the working fluid vapors at the adsorbent releases heat into an external environment. Regeneration of the adsorbent is then carried out with low temperature waste or solar heat to complete the cycle. While a number of working fluids could be employed, water is generally the most economically viable and environmentally benign option. The MOFs describe herein may be utilized as the porous absorbent material. In some embodiments, the MOF is porous.

In some embodiments, an MOF has a high water uptake capacity. As will be known to those of ordinary skill in the art, water uptake capacity is generally described as a function of relative water pressure and/or relative humidity. Those of ordinary skill in the art will be aware of methods for determining the water uptake capacity, for example, by determining a water adsorption isotherm for an MOF, wherein the uptake of water as a function of water pressure and/or humidity is determined. In some cases, the MOF has a high water uptake at low relative humidity. In some embodiments, at a relative water pressure of about 0.4 (e.g., about 40% relative humidity), the water uptake is at least about 0.2 g of water per gram of material (e.g., per gram of MOF), or at least about 0.3, or at least about 0.4, or at least about 0.5, or at least about 0.6, or great. In some cases, the water uptake is at between about 0.2 and about 2 g of water per gram of material (e.g., per gram of MOF), or between about 0.2 and about 1.5, or between about 0.2 and about 1.0, or between about 0.3 and about 2, or between about 0.3 and about 1.5, or between about 0.3 and about 1. Other ranges and values are also possible.

Definitions

For convenience, certain terms employed in the specification, examples, and appended claims are listed here.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s).

Definitions of specific functional groups and chemical terms are described in more detail below. For purposes of this invention, the chemical elements are identified in accordance with the Periodic Table of the Elements, CAS version, *Handbook of Chemistry and Physics,* 75*th* Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclochexyl.

The term "alkylene" as used herein refers to a bivalent alkyl group. An "alkylene" group is a polymethylene group, i.e., —$(CH_2)_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substituents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substituents, i.e., the substitutes recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The terms "halo" and "halogen" as used herein refer to an atom selected from the group consisting of fluorine, chlorine, bromine, and iodine.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

EXAMPLES

Working Example 1

This example describes the preparation and use of porous metal-organic frameworks (MOFs), comprising of organic compounds coordinated to metal ions, with tunable hydrophilic properties. The MOFs may be used as water adsorbents for adsorption heat pumping and storage applications. In the utilized methods, the combination of an organic compound containing N-heterocyclic ligating groups and divalent metal ions generate porous metal-organic frameworks with hydrophobic character that are stable to water (e.g., a requirement in adsorbents used in water adsorption applications). Treatment of these materials with chemical oxidizing agents renders them more hydrophilic by chemically modifying functional groups which are covalently attached to the organic compound and exposed within the interior pores/channels of the metal-organic framework materials. The increased hydrophilicity of the chemically treated metal-organic framework materials resulted in changes in the water adsorption profile of the modified versus parent materials. Such changes are generally desirable in water adsorption applications such as heat pumping and storage.

Methods:

The reaction of 4-amino-3,5-dimethylpyrazole with 1,4,5,8-naphthalenetetracarboxylic dianhydride or 2,6-dibromo-1,4,5,8-naphthalenetetracarboxylic dianhydride is used to generate the organic ligands/ligand precursors 1 and 2 (FIG. 1). Compound 2 reacts with $EtNH_2$ and Na(SEt) to generate compounds 3 and 4, respectively (FIG. 1).

Figure 2:
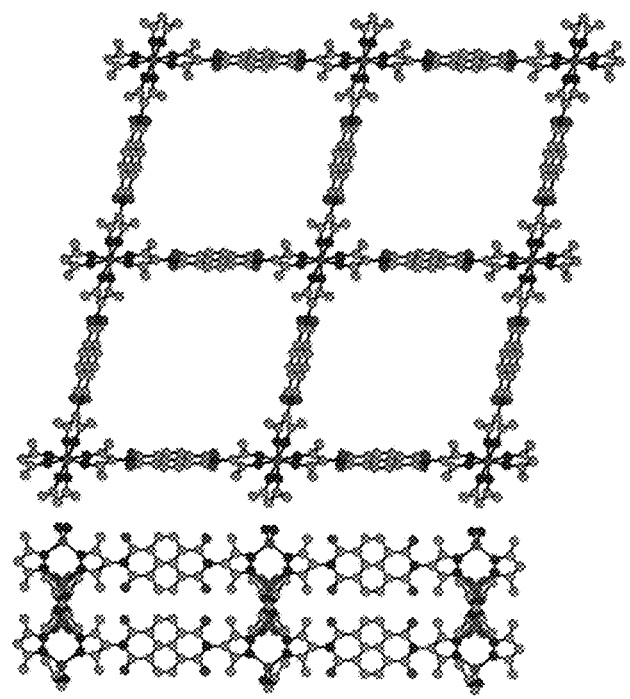
FIG. 2 shows a simulated structure of a non-limiting MOF, according to some embodiments.

Compounds 1, 3, or 4 were reacted with $Zn(NO_3)_2 \cdot 6H_2O$ in N,N-dimethylformamide (DMF) at 130° C. and afforded metal-organic framework materials 5, 6, and 7, respectively, as microcrystalline powders. The structures of 5, 6, and 7 comprised of chains of tetrahedral $Zn^{2+}$ ions bridged by pyrazolate groups and containing ~16 Å-wide channels with naphthalenediimide linker groups lining the channel surface (e.g., see FIG. 2). Metal-organic framework 5 showed no loss of crystallinity after immersion in water for 24 hours, suggesting a high degree of hydrolytic stability. Thermogravimetric analysis (TGA) of 5, 6, and 7 indicated that the onset of thermal decomposition occurs around 500° C., 450° C. and 350° C., respectively, suggesting a high degree of thermal stability for these materials. Apparent Brunauer-Emmett-Teller (BET) surface areas of 1460 $m^2$ $g^{-1}$, 1236 $m^2$ $g^{-1}$, and 888 $m^2$ $g^{-1}$, for 5, 6, and 7, respectively, were calculated from $N_2$ adsorption isotherms measured at 77 K on samples activated by heating in vacuum ($10^{-4}$-$10^{-5}$ torr) at 140-160° C. for 24 h. In FIG. 2: Simulated structure of 1.

Figure 3A:
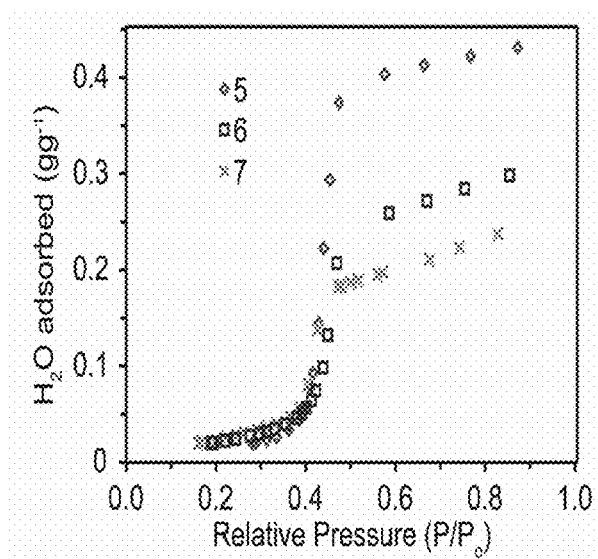
FIGS. 3a and 3b show water adsorption isotherms for non-limiting MOFs, according to some embodiments.
Figure 3B:
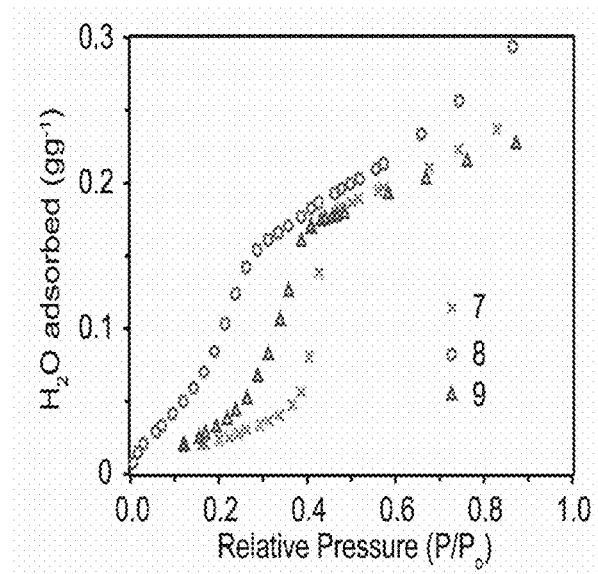

Water adsorption isotherms for evacuated samples of 5, 6, and 7 were measured volumetrically at 293 K (e.g., see FIG. 3b). The materials all exhibited Type V isotherms and showed little water adsorption over the relative humidity range $P/P_o$=0-0.4, but experienced sharp increases in water uptake at $P/P_o$=0.4-0.5 (~6.9-8.7 torr).

Chemical oxidation of the ethyl sulfide groups in 7 to generate materials containing ethyl sulfoxide and ethyl sulfone functional groups was used to alter hydrophilicity and the relative humidity at which the water adsorption step occurs. Metal-organic framework 7 was allowed to react with either 2 eq or 8 eq of dimethyldioxirane in acetone at −20° C. to generate the chemically oxidized metal-organic frameworks 8 and 9, respectively. Powder X-ray diffraction experiments confirmed that 8 and 9 retain crystallinity and were structurally similar to the parent material 7. $^1$H NMR spectroscopic measurements of acid digested samples and infrared spectroscopy experiments on the crystalline powders confirmed that chemical oxidation of the ethyl sulfide groups occurs to generate ethyl sulfoxide and ethyl sulfone functional groups. Using these characterization methods, 8 was determined to contain a mixture of functional groups in the ratio 1:8:1 sulfide:sulfoxide:sulfone while 9 contains a 2:8 sulfoxide:sulfone mixture.

Thermogravimetric analysis (TGA) of 8 and 9 indicates that the onset of thermal decomposition occurs around 500° C. and 350° C., respectively, suggesting a high degree of thermal stability for these materials. Samples of 8 and 9 heated at 50° C. and 100° C., respectively, under vacuum exhibit apparent BET surface areas of 927 m$^2$ g$^{-1}$ and 764 m$^2$ g$^{-1}$, respectively. PXRD analysis of 8 and 9 after heating under vacuum at these temperatures indicate that bulk crystallinity is maintained. $^1$H NMR spectroscopy of acid digested samples of 8 and 9 after heating under vacuum at these temperatures showed retention of the sulfoxide and sulfone functionalities.

Water adsorption isotherms for evacuated samples of 8 and 9 were measured volumetrically at 293 K (e.g., see FIG. 3b). These measurements show that water uptake steps occur around $P/P_o$=0.2-0.3 (~3.5-5.2 torr) for 8 and 0.3-0.4 (~5.2-7.0 torr) for 9 The water uptake steps observed for 8 and 9 are shifted to lower relative humidity versus that observed for 7.

The methods carried out in this example may be used to generate metal-organic framework structures with water adsorption properties suitable for heat storage or heat pumping applications. In the case of hydrophobic materials, low regeneration temperatures may allow for the use of low-temperature waste heat or solar collectors as energy sources. Alternatively, materials engineered to be more hydrophilic may function under more extreme conditions (e.g., provide lower cooling temperatures and/or adsorb water at higher external temperatures) and/or achieve large water exchange capacities over a desired working pressure/temperature range.

Without wishing to be bound by theory, the following discussion relates to how the position of the water uptake step in chemically modified materials 7, 8, and 9 may modulate their performance in a water-based adsorption heat pumping system. In the working cycle of an adsorption chiller, heat is generally transferred by the evaporation of water at a cooling application temperature ($T_{evap}$) and the adsorption of water by the adsorbent at a temperature ($T_{ads}$). In order to realize efficient cooling to a desired $T_{evap}$, it is desirable for the adsorbent to reach a high water loading at a relative humidity, ($P/P_o$), less than or equal to $P_{evap}/P_{sat}(T_{ads})$, where $P_{sat}(T_{ads})$ is the saturation pressure corresponding to a temperature of $T_{ads}$. This condition generally depends on both the adsorbent temperature $T_{ads}$ and the intrinsic water adsorption profile of the adsorbent. Therefore, the relative humidity at which water adsorption occurs at the adsorbent is based, at least in part, on the minimum temperature for cooling, $T_{evap}$, and the maximum allowable adsorbent temperature, $T_{ads}$. As described herein, 7, 8, and 9 experienced steep adsorption steps just prior to $P/P_o$ values of 0.466, 0.312, and 0.431, respectively. At these relative humidities, similar water loadings of 0.166, 0.175, and 0.178 gg$^{-1}$ may be achieved. However, for a fixed $T_{ads}$ of 40° C., 7, 8, and 9 may maintain different minimum cooling temperatures ($T_{evap}$) of 26.4° C., 19.8° C., and 25.1° C., respectively, at these loadings. Conversely, for a $T_{evap}$=20° C. cooling application, these materials may be most efficiently function as adsorbents at $T_{ads}$≤32.9° C., 40.3° C., and 34.3° C., respectively. The calculated working temperatures achieved by these materials are relevant for applications around room temperature.

TABLE 1

Observed water loading lifts after initial water adsorption step and calculated minimum $T_{evap}$ and maximum $T_{ads}$ values based on the corresponding $P/P_0$ values.

|   | lift (gg$^{-1}$) (@ $P/P_0$) | min $T_{evap}$ ($T_{ads}$ = 40° C.) | max $T_{ads}$ ($T_{evap}$ = 20° C.) |
|---|---|---|---|
| 7 | 0.166 (0.466) | 26.4° C. | 32.9° C. |
| 8 | 0.175 (0.312) | 19.8° C. | 40.3° C. |
| 9 | 0.178 (0.431) | 25.1° C. | 34.3° C. |

Prophetic Example 1

The approach of using functional groups or modification of functional groups decorating the pore/channel interiors of metal-organic frameworks to tune the hydrophilicity and water adsorption behaviours, including water exchange capacity and relative humidity at which water adsorption occurs, of these materials for water adsorption applications as described in working Example 1 may be modified to include:

a) The use of other divalent metal ions including, but not limited to, Mg$^{2+}$, Mn$^{2+}$, Fe$^{2+}$, Co$^{2+}$, Ni$^{2+}$, and Cu$^{2+}$.

b) The use of ligands with other N-heterocyclic metal binding groups including, but not limited to, as pyridines, imidazoles, triazoles, or tetrazoles. Such nitrogen-based ligand binding groups in conjunction with divalent metal ions may confer water stability to the resulting metal-organic frameworks.

c) The use of linearly extended or branched ligands with similar N-containing end groups (e.g., heterocycles). The structure of such ligands may include the presence of a single or series of alkyl or aryl spacers between the imide N-atom and the N-heterocyclic binding group.

d) The use of linkers other than 1,4,5,8-naphthalenetetracarboxylic diimide to bridge the N-heterocyclic metal binding groups, including, but not limited to, benzene-1,2,4,5-tetracarboxylic diimide, 1,4-phenylene, 4,4'-biphenyl, and polycarboxylic anhydrides with trigonal and other branched geometries.

e) The inclusion of other hydrophilic/hydrophobic functional groups about the pore/channel surface to modify the water uptake properties. Non-limiting examples of such groups include: —NR$_2$, —OR, —COOR, —PO(OR)$_3$, —NR$_3^+$, SR, S(O)R, and SO$_2$R (e.g., R═H, alkyl, aryl).

Post-synthetic modification of these or other functional groups within metal-organic frameworks. Such modification may be completed to modify may be completed to hydrophilicity and/or water adsorption properties of the materials including, but not limited to, the water exchange capacity and relative humidity at which water adsorption occurs. For example, oxidation of other alkyl or aryl sulfide groups (—SR, R=H, methyl, propyl, butyl, phenyl, etc.) to generate mixtures of sulfide, sulfoxide, and sulfone groups, may be carried out).

Pyrazolate-based materials represent a rare, water stable class of metal-organic frameworks whose potential in water adsorption applications has not been fully recognized. Such stability may be extended to metal-organic frameworks derived from ligands containing other N-heterocyclic metal binding groups.

The use of organic ligand functional groups or postsynthetic chemical modification techniques to modulate hydrophilicity has the potential to produce MOF adsorbents which exhibit varying degrees of hydrophilicity. Such precise chemical control is difficult to achieve with currently used silica and zeolite materials.

Working Example 2

Figure 5:
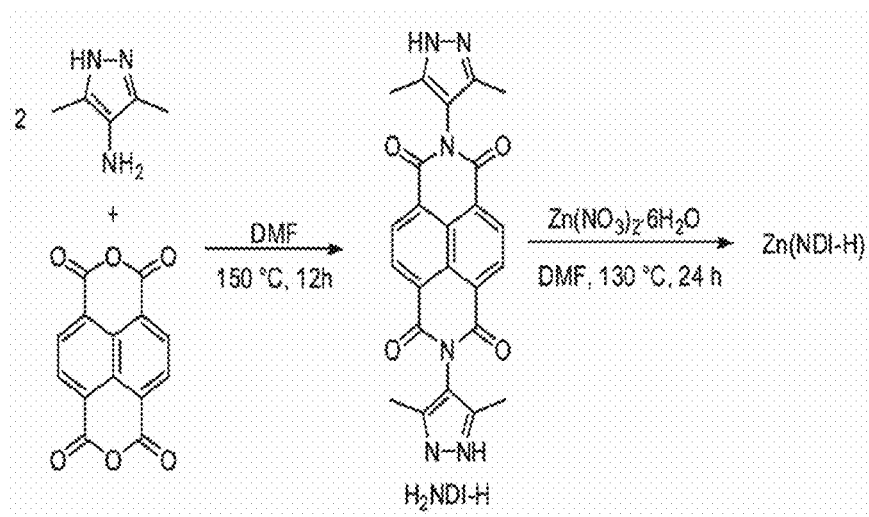
FIGS. 5 and 7 illustrates the synthesis of a non-limiting MOF, according to some embodiments.

In FIG. 4: Diagram of an intermittent adsorption cooling process. In FIG. 5: Synthesis of $H_2NDI$—H and Zn(NDI—H) (also referred to as 5 in working example 1).

Results and Discussion: A modular synthesis involving the condensation of 4-amino-3,5-dimethylpyrazole with linear arene dianhydrides was employed. This route allows for multigram scale synthesis of dipyrazole ligands from commercially available precursors as well as facile access to functionalized derivatives.

Figure 6:
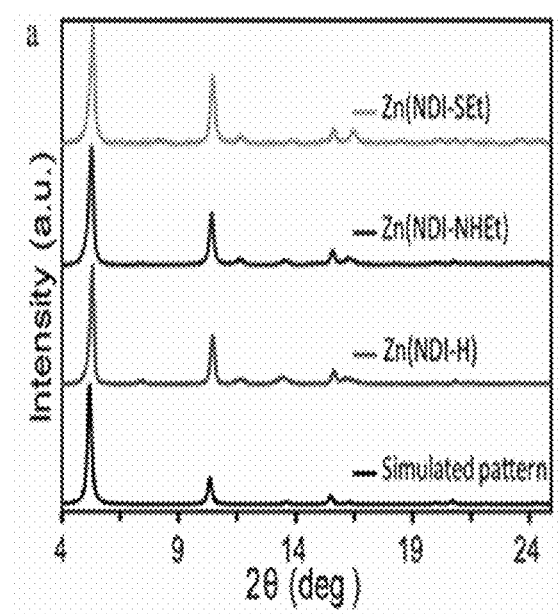
FIG. 6 shows powder X-ray diffraction patterns of a non-limiting MOF, according to some embodiments.

The new dipyrazole ligand $H_2NDI$—H was synthesized by condensation of 2 equivalents of 4-amino-3,5-dimethylpyrazole with naphthalene dianhydride in DMF (FIG. 5). Subsequent reaction of $H_2NDI$—H with $Zn(NO_3)_2 \cdot 6H_2O$ in N,N-dimethylformamide (DMF) at 130° C. afforded Zn(NDI—H) as a microcrystalline yellow powder. The powder X-ray diffraction (PXRD) pattern of Zn(NDI—H) closely matched a pattern simulated from a structural model based on Co(dmdpb) (dmdpb=1,4-bis[(3,5-dimethyl)dipyrazol-4-ylbenzene), suggesting a common structure type consisting of long chains of tetrahedral $Zn^{2+}$ ions bridged by pyrazolate groups. However, breathing distortions in which variation in the angle (θ) made between two ligands at a metal node results in oblique rather than square channels are known to occur in dipyrazolate-based MOFs. To model this type of distortion, an original visual fitting routine, MOF-FIT, implemented in MATLAB was developed, which allows determination of breathing angles and other translational MOF deformations by dynamically simulating structures with varying θ input angles and visually comparing the results in calculated and experimental PXRD patterns. Using this method, we found that the experimental pattern of Zn(NDI-H) was found more closely matched that of a model structure with a breathing angle (θ) of 77° rather than 90° (FIG. 6). A simulated structure (e.g., see FIG. 2) indicates that Zn(NDI—H) contains ~16 Å-wide channels with naphthalenediimide linker groups lining the channel surface.

In agreement with the expected microporous structure, thermogravimetric analysis (TGA) showed the loss of ~4 DMF guest solvent molecules per formula unit upon heating to 140° C. and a subsequent mass loss occurring at ~500° C., likely indicative of decomposition of the framework. An apparent Brunauer-Emmett-Teller (BET) surface area of 1460 $m^2$ $g^{-1}$ was calculated from a $N_2$ adsorption isotherm measured at 77 K on a sample of Zn(NDI—H) activated by heating in vacuum ($10^{-4}$-$10^{-5}$ torr) at 160° C. for 24 h (FIG. 3a). In line with the exceptional hydrolytic stability observed for other pyrazolate-based MOFs, no significant changes were observed in the PXRD pattern of Zn(NDI—H) after immersion in water for 24 h. In FIG. 6: Powder X-ray diffraction patterns of Zn(NDI—X) (X=H, NHEt, SEt).

Modification of the naphthalene core of the dipyrazole ligands in Zn(NDI—H) could provide a convenient means to study the effects of pore hydrophilicity on the water adsorption characteristics of pyrazolate-based MOFs. Conveniently, nucleophilic aromatic substitution of core-halogenated NDIs has been used to install a variety of functional groups at the naphthalene core. Thus, the dibrominated dipyrazole $H_2NDI$—Br (also referred to as 2 in working example 1) was synthesized and found that it reacted cleanly with $EtNH_2$ and Na(SEt) to generate the new dipyrazole ligands $H_2NDI$—NHEt and $H_2NDI$—SEt, respectively (FIG. 2). Subsequent reaction of $H_2NDI$—NHEt (also referred to as 3 in Working Example 1) and $H_2NDI$—SEt (also referred to as 4 in Working Example 1) with $Zn(NO_3)_2 \cdot 6H_2O$ in DMF at 130° C. afforded Zn(NDI—NHEt) and Zn(NDI-SEt) as blue and red/orange microcrystalline powders, respectively. PXRD analysis of Zn(NDI—NHEt) (also referred to as 6 in Working Example 1) and Zn(NDI—SEt) (also referred to as 7 in Working Example 1) confirmed their isostructural relationship with Zn(NDI—H). The TGA profiles of Zn(NDI—NHEt) and Zn(NDI—SEt) showed the loss of DMF guest solvent molecules up to 140° C. and the apparent onset of decomposition at around 450° C. and 350° C., respectively. $N_2$ adsorption isotherms measured at 77 K on samples of Zn(NDI—NHEt) and Zn(NDI—SEt) activated by heating in vacuum at 140° C. for 24 h gave apparent BET surface areas of 1236 $m^2$ $g^{-1}$ and 888 $m^2$ $g^{-1}$, respectively (FIG. 3a). The lower values observed for these relative to Zn(NDI—H) may be attributed to the functional groups that partially block the pores of the substituted materials.

The volumetric water adsorption isotherms for evacuated samples of Zn(NDI—H), Zn(NDI—NHEt), and Zn(NDI—SEt) were measured at 293 K and are shown in FIG. 3b. These materials all exhibited Type V isotherms and showed little water adsorption over the relative humidity range $P/P_o$=0-0.4, but experienced sharp increases in water uptake at $P/P_o$=0.4-0.5 (~6.9-8.7 torr). This behavior is similar to that observed for water adsorption in activated carbons and suggests largely hydrophobic character for the interior surface of the MOF channels. More notably, these observations are in agreement with the similarity of the hydrophobic parameters (π) for the ligand substituents —H (0.00), —NHEt (0.08), and —SEt (+1.07) exposed at the MOF channel surface.

In light of these results, other means to alter the hydrophilicity of the functional groups decorating the channel interior and examine the ensuing effects on the water adsorption step were investigated. Consequently, postsynthetic oxidation of the sulfide groups decorating the channel interior of Zn(NDI—SEt) was investigated to generate more polar and hydrophilic sulfoxide (—SOEt, π=−1.04) and sulfone ($SO_2Et$, π=−1.09) groups. Treatment of red-orange suspensions of Zn(NDI—SEt) in acetone with either 2 eq or 8 eq of dimethyldioxirane at −20° C. resulted in gradual color changes to afford orange-yellow Zn(NDI—SOEt) (also referred to as 8 in Working Example 1) and yellow Zn(NDI—$SO_2Et$) (also referred to as 9 in Working Example 1) respectively. After filtration and washing with fresh acetone, powder X-ray diffraction confirmed that the crystallinity of both samples was retained without any significant structural changes. The IR spectrum of Zn(NDI—SOEt) showed the appearance of two new bands: a strong band at 1047 cm$^{-1}$ and a weak band at 1136 cm$^{-1}$, corresponding to the formation of sulfoxide and sulfone groups, respectively. The IR spectrum of Zn(NDI—SO$_2$Et) displayed a new signal at 1236 cm$^{-1}$, suggesting the predominant conversion of the sulfide groups to sulfones. The $^1$H NMR spectra of samples of Zn(NDI—SOEt) and Zn(NDI—SO$_2$Et) digested in mixtures of DMSO-d$_6$, DCI, and D$_2$O were measured to quantify the degree of oxidation of the sulfide groups. The spectrum of Zn(NDI—SOEt) showed a mixture of products in the ratio 1:8:1 sulfide:sulfoxide:sulfone while that of Zn(NDI—SO$_2$Et) indicated nearly complete oxidation of the sulfide to give a 2:8 sulfoxide:sulfone mixture.

Figure 7:
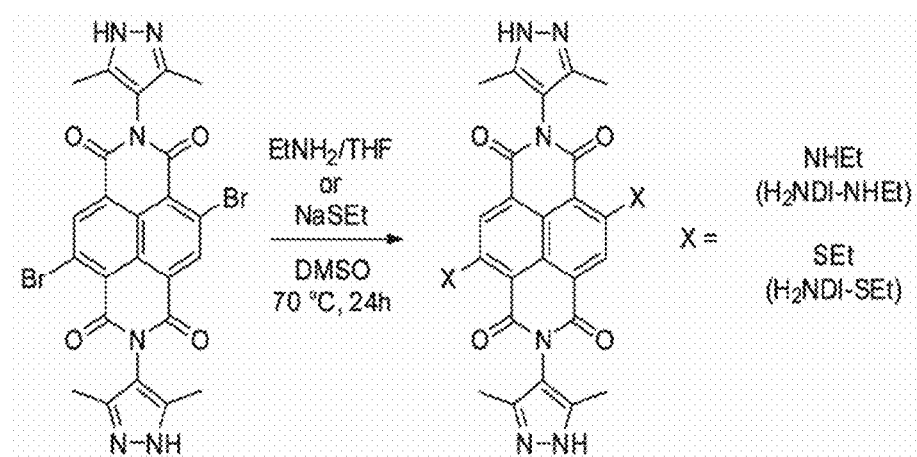

The TGA profile of Zn(NDI—SOEt) showed two distinct mass losses up to 180° C., with continuing gradual decrease in mass up to the apparent framework decomposition at around 500° C. while that of Zn(NDI—SO$_2$Et) exhibited loss of guest solvent molecules up to 115° C. and the apparent onset of framework decomposition. In FIG. 7: Synthesis of H$_2$NDI—EtNH and H$_2$NDI—SEt.

Samples of Zn(NDI—SOEt) and Zn(NDI—SO$_2$Et) activated at 50° C. and 100° C. under vacuum exhibited apparent BET surface areas of 927 m$^2$ g$^{-1}$ and 764 m$^2$ g$^{-1}$, respectively in line with that of Zn(NDI—SEt) (888 m$^2$ g$^{-1}$). PXRD analysis of these samples after activation indicated that bulk crystallinity was maintained while the $^1$H NMR spectra of acid digested samples showed retention of the sulfoxide and sulfone functionalities.

The water uptake steps of the adsorption isotherms for activated samples of Zn(NDI—SOEt) and Zn(NDI—SO$_2$Et), shown in FIG. 5b along with Zn(NDI—SEt) for comparison, are shifted to lower relative humidity of around P/P$_o$=0.2-0.3 (~3.5-5.2 torr) for Zn(NDI—SOEt) and 0.3-0.4 (~5.2-7.0 torr) for Zn(NDI—SO$_2$Et). While these shifts are in agreement with the greater hydrophilicity of the —SOEt and —SO$_2$Et groups versus —SEt, the water adsorption step for Zn(NDI—SOEt) is clearly shifted from that of Zn(NDI—SO$_2$Et) despite similar hydrophobic parameters for the —SOEt (-1.04) and —SO$_2$Et (-1.09) groups. However, these hydrophobic parameters, derived from water-octanol partitioning, differ from hydrophilicity data determined in other solvent mixtures. Namely, partition coefficients determined from water-alkane mixtures (log P$_{alk}$) for methyl phenyl sulfoxide (log P$_{alk}$=-1.52) and methyl phenyl sulfone (log P$_{alk}$=-0.87) suggest that sulfoxides exhibit greater hydrophilic character than sulfones in highly hydrophobic environments. This behavior corroborates the larger shift observed for the water adsorption step of Zn(NDI—SOEt) versus Zn(NDI—SO$_2$Et) given the otherwise hydrophobic character of the MOF channel interior.

Working Example 3

The following example provides additional supporting experimental details for Working Examples 1 and 2.

General Considerations. 1,4,5,8-Naphthalenetetracarboxylic dianhydride (TCI), 3,5-dimethylpyrazole (Aldrich), 2 M ethylamine/THF (Alfa Aesar), sodium ethanethiolate (Fluka), Zn(NO$_3$)$_2$.xH$_2$O (Alfa Aesar), N,N-dimethylformamide (DMF, 99.8%, VWR), and dimethylsulfoxide (DMSO, Aldrich) were used as received unless otherwise noted. 2-amino-3,5-dimethylpyrazole, 2,6-dibromo-1,4,5,8-naphthalenetetracarboxylic dianhydride, and dimethyldioxirane (~0.09M in acetone) were prepared according to literature procedures. Powder X-ray diffraction patterns were collected on a Bruker Advance D8 diffractometer using Nickel-filtered Cu-K$_\alpha$ radiation ($\lambda$=1.5418 Å). Powder X-ray diffraction samples were prepared by placing a thin layer of sample on a zero-background silicon plate. IR spectra were collected using a Bruker Tensor 37 FTIR spectrometer equipped with a Pike Ge ATR accessory. Thermogravimetric analysis (TGA) was performed on a TA Instruments Q500 Thermogravimetric Analyzer at a heating rate of 2 or 4° C./min under a nitrogen gas flow of 90 mL/min. Elemental analyses were performed at Complete Analysis Laboratories, Inc (Parsippany, N.J.).

Gas sorption measurements. A Micromeritics ASAP 2020 Surface Area and Porosity Analyzer was used to measure N$_2$ and H$_2$O adsorption isotherms. Oven-dried sample tubes equipped with TranSeals™ (Micrometrics) were evacuated and tared. Samples (100-200 mg) were transferred to the sample tube, which was then capped by a TranSeal™. Samples were heated to the appropriate temperatures and held at those temperatures until the outgas rate was less than 2 mTorr/minute. The evacuated sample tubes were weighed again, and the sample mass was determined by subtracting the mass of the previously tared tubes. N$_2$ isotherms were measured using a liquid nitrogen bath (77 K). H$_2$O isotherms were measured at 293 K using a circulating water bath with temperature control provided by a Neslab LT-50DD refrigerated circulating bath. Ultra high purity grade (99.999% purity) N$_2$ and He, oil-free valves and gas regulators were used for all free space corrections and measurements.

Simulation of PXRD pattern from Zn(NDI-H) model structure. A model structure of Zn(NDI-H) was constructed starting from the reported X-ray crystal structure of Co(bdpb) (bdpb$^{2-}$=1,4-bis[(3,5-dimethyl)pyrazol-4-yl]benzene). The bdpb$^{2-}$ organic linker was replaced with [NDI—H]$^{2-}$ using Discovery Studio and the unit cell lengths a and b were increased to 24.5 Å to accommodate the extended linker while the c axis length (7.16 Å) and cell angles ($\alpha=\beta=\gamma=90°$) were left unchanged. The powder X-ray diffraction pattern of the structure was dynamically simulated as a function of breathing angle ($\theta$), defined as the angle made between ligands connected by the metallic vertex, using the original fitting routine MOF-FIT that allows determination of breathing angles and other translational MOF deformations by visually matching powder experimental powder X-ray diffraction patterns with ones predicted by manual modulation of unit cell parameters, and implemented in MATLAB. Using the dynamic modeling function, a structure with a breathing angle of $\theta$=77° was found to provide the best visual fit of the experimental pattern of Zn(NDI—H). The unit cell parameters of the final structure were a=22 Å, b=27 Å, c=7 Å and $\alpha=\beta=\gamma=90°$. The final powder X-ray diffraction pattern of the model structure was simulated using Mercury 2.4.5.

Synthesis of H$_2$NDI—H. A dry 100 mL Schlenk flask was charged with 1,4,5,8-Naphthalenetetracarboxylic dianhydride (0.86 g, 3.2 mmol), 3,5-dimethylpyrazole (0.75 g, 6.8 mmol), and anhydrous DMF (50 mL) under a nitrogen atmosphere. The reaction mixture was heated at 150° C. with rapid stirring for 8 hrs. The flask was cooled to room temperature and the dark brown DMF solution was poured into stirring diethyl ether (150 mL). The precipitated yellow solid was separated by filtration and recrystallized from DMF/diethyl ether (10 mL: 20 mL). The product was filtered and dried in vacuo at 70° C. to afford 1.2 g (82%) of light yellow powder. $^1$H NMR (399.43 MHz; dmso-d$_6$): $\delta$ 1.97 (s, 6H, pyrazole-CH$_3$), 2.06 (s, 6H, pyrazole-CH$_3$), 8.74 (s, 4H, naph-CH), 12.51 (s, 2H, pyrazole-NH). $^{13}$C NMR (399.43

MHz; dmso-d$_6$): δ 9.00, 11.38, 111.98, 126.73, 130.82, 136.16, 144.52, 162.28. Elemental analysis calcd. for C$_{24}$H$_{18}$N$_6$O$_4$: C, 63.43; H, 3.99; N, 18.49. Found: C, 63.38; H, 3.81; N, 18.58.

Synthesis of H$_2$NDI-Br. A dry 100 mL Schlenk flask was charged with 2,6-dibromo-1,4,5,8-naphthalenetetracarboxylic dianhydride (1.0 g), 3,5-dimethylpyrazole (0.44 g, 4.6 mmol), and acetic acid (50 mL). The reaction mixture was heated to reflux with rapid stirring for 8 hrs. The flask was cooled to room temperature, and the precipitated yellow solid was separated by filtration and washed with water (3×10 mL) and hot methanol (3×100 mL). The product was dried in vacuo at 70° C. to afford 0.65 g (53%) of yellow-orange powder that was used without further purification. $^1$H NMR (399.43 MHz; dmso-d$_6$): δ 2.02 (s, 12H, pyrazole-CH$_3$), 8.79 (s, 2H, naph-CH), 12.47 (s, 2H, pyrazole-NH).

Synthesis of H$_2$NDI-NHEt. A 20 mL scintillation vial was charged with H$_2$NDI—Br (0.65 g, 1.06 mmol), DMSO (10 mL), and 2 M ethylamine/THF (6.0 mL, 12 mmol). The vial was sealed, and the mixture was heated at 70° C. with rapid stirring for 24 hrs. The vial was allowed to cool to room temperature, and the reaction mixture was poured into stirring water (100 mL). The precipitated blue/purple solid was separated by filtration and washed with water (3×10 mL) and methanol (3×5 mL). The product was purified by multiple recrystallizations from hot dichloromethane/methanol (15 mL: 45 mL) to afford 0.240 g (42%) of H$_2$NDI—NHEt as a blue-purple microcrystalline solid. $^1$H NMR (399.43 MHz; dmso-d$_6$): δ 1.31 (t, 6H, NH—CH$_2$—CH$_3$, $^3$J$_{H-H}$=7.2 Hz), 1.93 (s, 6H, pyrazole-CH$_3$), 2.02 (s, 6H, pyrazole-CH$_3$), 3.53 (m, 4H, NH—CH$_2$—CH$_3$), 8.09 (s, 2H, naph-CH), 9.19 (s, 2H, NH—CH$_2$—CH$_3$), 12.45 (s, 2H, pyrazole-NH). $^{13}$C NMR (399.43 MHz; dmso-d$_6$): δ 8.94 (pyrazole-CH$_3$), 11.23 (pyrazole-CH$_3$), 14.43 (—NHCH$_2$CH$_3$), 37.07 (—NHCH$_2$CH$_3$), 101.25, 112.23, 118.2, 121.19, 125.90, 148.53, 161.96, 165.16. Elemental analysis calcd. for (C$_{28}$H$_{28}$N$_8$O$_4$): C, 62.21; H, 5.22; N, 20.73. Found: C, 61.43; H, 5.15; N, 20.4.

Synthesis of H$_2$NDI-SEt. A dry 50 mL Schlenk flask was charged with H$_2$NDI—Br (0.64 g, 1.04 mmol), sodium ethanethiolate (0.35 g, 3.57 mmol), and DMSO (10 mL). The reaction mixture was heated at 70° C. with rapid stirring for 24 hrs. The flask was cooled to room temperature and the reaction mixture was poured into stirring water (100 mL). The precipitated orange-red solid was separated by filtration and washed with water (3×10 mL) and methanol (3×5 mL). The product was purified by multiple recrystallizations from hot dichloromethane/methanol (45 mL: 15 mL) to afford 0.40 g (66%) of H$_2$NDI—SEt as an orange microcrystalline solid. $^1$H NMR (399.43 MHz; dmso-d$_6$): δ 1.41 (t, 6H, S—CH$_2$—CH$_3$, $^3$J$_{H-H}$=7.34 Hz), 2.00 (s, 6H, pyrazole-CH$_3$), 3.26 (q, 4H, S—CH$_2$—CH$_3$, $^3$J$_{H-H}$=7.34 Hz), 8.62 (s, 2H, naph-CH), 12.45 (br s, 2H, pyrazole-NH). $^{13}$C NMR (399.43 MHz; dmso-d$_6$): δ 9.05, 11.29, 12.84, 25.25, 111.94, 119.22, 124.18, 125.29, 127.53, 147.28, 161.60, 162.38. Elemental analysis calcd. for C$_3$H$_7$NO)$_{0.5}$: C, 58.52; H, 4.56; N, 14.62. Found: C, 58.57; H, 4.63; N, 14.61.

Synthesis of Zn(NDI-X) (X=H, NHEt, SEt). A dry 100 mL Schlenk flask was charged with H$_2$NDI—H (0.64 g, 1.4 mmol), Zn(NO$_3$)$_2$.6H$_2$O (0.46 g, 1.5 mmol), and DMF (160 mL) under a nitrogen atmosphere. The reaction mixture was heated at 130° C. for 24 hrs. After allowing the reaction to cool to room temperature, the precipitated yellow solid was separated by filtration, washed with DMF (3×5 mL), and air dried to afford 0.97 g of Zn(NDI—H).xDMF as light yellow powder. Zn(NDI—NHEt) and Zn(NDI—SEt) were prepared analogously. Samples for combustion elemental analysis (C, H, N) activated by heating to 140-160° C. under high vacuum (<10$^{-4}$ torr) for at least 24 h. Zn(NDI-H): Elemental analysis calcd. for (ZnC$_{24}$H$_{16}$N$_6$O$_4$): C, 55.67; H, 3.11; N, 16.23. Found: C, 54.55; H, 3.15; N, 16.37. Zn(NDI—NHEt): Elemental analysis calcd. for (ZnC$_{28}$H$_{26}$N$_8$O$_4$): C, 55.68; H, 4.34; N, 18.55. Found: C, 53.44; H, 4.07; N, 18.46. Zn(NDI—SEt): Elemental analysis calcd. for (ZnC$_{28}$H$_{24}$N$_6$O$_4$S$_2$): C, 52.71; H, 3.79; N, 13.17. Found: C, 52.56; H, 3.63; N, 13.15.

Oxidation of Zn(NDI—SEt) with DMDO. A solution of dimethyldioxirane (5.3 mL, 0.09 M in acetone) was added over 30 min to a stirring suspension of Zn(NDI—SEt) (0.15 g) in acetone (20 mL) at −20° C. The mixture was allowed to warm to room temperature and stirred for 12 hrs. The solid was separated by filtration, washed with acetone (5×10 mL), and air-dried to afford 0.12 g of yellow powder. The extent of oxidation of the sulfide groups was determined by measuring the IR spectrum of the recovered solid and the $^1$H NMR spectrum of a sample (~15 mg) digested with a dmso-d$_6$ (0.6 mL) and DCl/D$_2$O (12 M, 0.05 mL) solvent mixture.

Synthesis of Zn(NDI-SO$_2$Et). A solution of dimethyldioxirane (20 mL, 0.09 M in acetone) was slowly added over 30 min to a stirring suspension of Zn(NDI—SEt) (0.15 g) in acetone (20 mL) at −20° C. The mixture was allowed to warm to room temperature and stirred for 12 hrs. The solid was separated by filtration, washed with acetone (5×10 mL), and air-dried to afford 0.12 g of yellow powder. Oxidation of the sulfide was confirmed by IR and measuring the $^1$H NMR spectrum of a sample of the product (~15 mg) after digestion in dmso-d$_6$ (0.6 mL) and DCl/D$_2$O (12 M, 0.05 mL).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:
1. A metal organic framework (MOF) comprising:
   a plurality of metal ions, each coordinated with at least one ligand, wherein each ligand has the structure [Q-(Ar)$_m$]$^{m-}$, wherein:

each Ar is the same or different and is an unsaturated N-heterocyclic aromatic group selected from the group consisting of pyrazolate, imidazolate, and tetrazolate;
m is 2; and
Q comprises the structure:

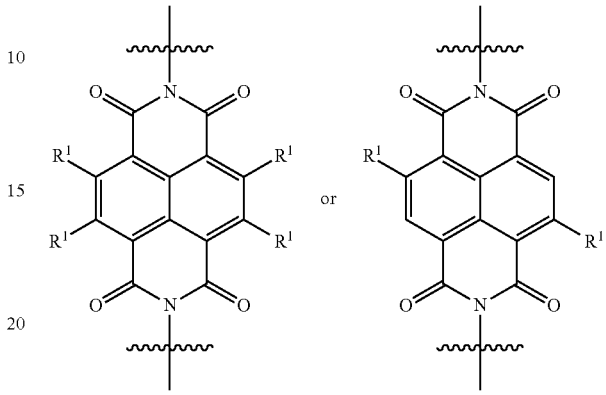

wherein each R$^1$ is the same or different and is selected from the group consisting of hydrogen, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$, wherein each R' is the same or different and is optionally substituted alkyl or optionally substituted aryl.

2. The MOF of claim 1, wherein a portion of the metal ions are associated with two, three, or four ligands, and each of those ligands is individually associated with two metal ions.

3. The MOF of claim 1, wherein a portion of the metal ions are associated with four ligands, and each of those ligand is individually associated with two metal ions.

4. The MOF of claim 1, wherein each unsaturated N-heterocyclic group is a pyrazolate group.

5. The MOF of claim 1, wherein each metal ion is a monovalent, divalent, or trivalent metal ion.

6. The MOF of claim 1, wherein each metal ion is selected from the group consisting of Ag$^+$, Cu$^+$, and Au$^+$.

7. The MOF of claim 1, wherein each metal ion is selected from the group consisting of Mg$^{2+}$, Mn$^{2+}$, Fe$^{2+}$, Co$^{2+}$, Ni$^{2+}$, Cu$^{2+}$, Pd$^{2+}$, Pt$^{2+}$, Ru$^{2+}$, Cd$^{2+}$, Zn$^{2+}$, Pb$^{2+}$, Hg$^{2+}$, V$^{2+}$, Cr$^{2+}$, and Ni$^{+2}$.

8. The MOF of claim 1, wherein each metal ion is Zn$^{2+}$.

9. The MOF of claim 1, wherein each metal ion is selected from the group consisting of Fe$^{3+}$, V$^{3+}$, Ti$^{3+}$, Sc$^{3+}$, Al$^{3+}$, In$^{3+}$, Ga$^{3+}$, Mn$^{3+}$, Co$^{3+}$, and Cr$^{3+}$.

10. The MOF of claim 1, wherein the ligand comprises the structure:

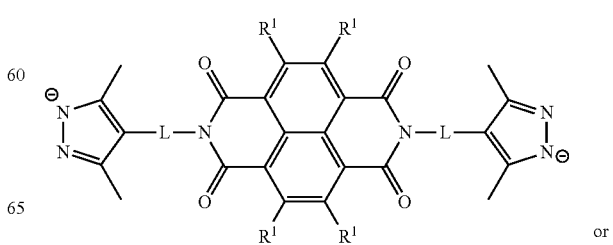

or

-continued

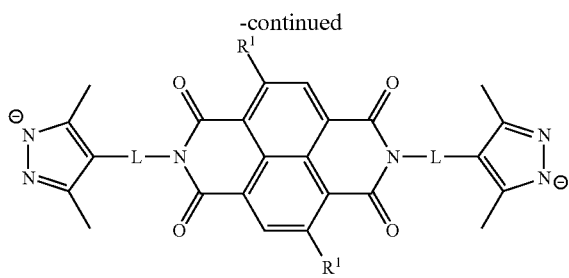

wherein:
  each $R^1$ is the same or different and is selected from the group consisting of hydrogen, —$NO_2$, —R', —F, —Cl, —Br, —I, —CN, —NC, —$SO_3$R', —$SO_3$H, —OR', —OH, —SR', —SH, —$PO_3$R', —$PO_3$H, —$CF_3$, —NR'$_2$, —NHR', and —$NH_2$;
  each L is the same or different and is absent or selected from the group consisting of optionally substituted alkylene, optionally substituted heteroalkylene, optionally substituted arylene, and optionally substituted heteroarylene; and
  each R' is the same or different and is optionally substituted alkyl or optionally substituted aryl.

11. The MOF of claim 10, wherein the ligand comprises the structure:

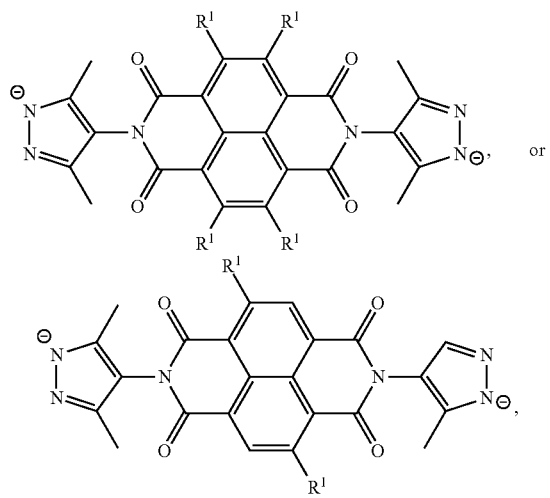

wherein:
  each $R^1$ is the same or different and is selected from the group consisting of hydrogen, —$NO_2$, —R', —F, —Cl, —Br, —I, —CN, —NC, —$SO_3$R', —$SO_3$H, —OR', —OH, —SR', —SH, —$PO_3$R', —$PO_3$H, —$CF_3$, —NR'$_2$, —NHR', and —$NH_2$; and
  each R' is the same or different and is optionally substituted alkyl or optionally substituted aryl.

12. The MOF of claim 10, wherein each $R^1$ is hydrogen, halide, NHR', or SR', wherein each R' is the same or different and is optionally substituted alkyl or optionally substituted aryl.

13. The MOF of claim 10, wherein each $R^1$ is hydrogen, Br, NHEt, or SEt.

14. The MOF of claim 1, wherein the MOF is porous.

15. A method, comprising:
  using an MOF for water adsorption, wherein the MOF comprising a plurality of metal ions, each coordinated with at least one ligand, wherein each ligand has the structure [Q-(Ar)$_m$]$^{m-}$,
  wherein each Ar is the same or different and is an unsaturated N-heterocyclic aromatic selected from the group consisting of pyrazolate, triazolate, and tetrazolate, m is 2, 3, or 4, and Q comprises the structure:

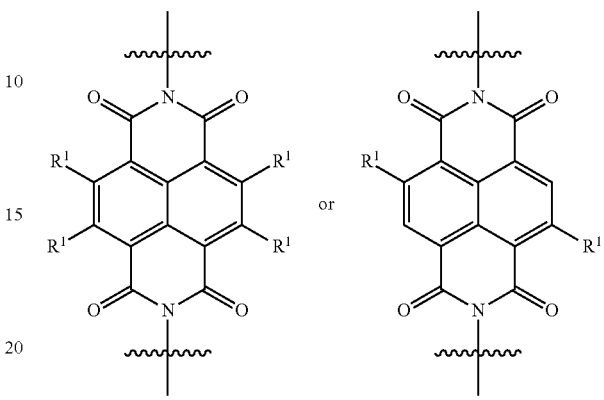

wherein each $R^1$ is the same or different and is selected from the group consisting of hydrogen, —$NO_2$, —R', —F, —Cl, —Br, —I, —CN, —NC, —$SO_3$R', —$SO_3$H, —OR', —OH, —SR', —SH, —$PO_3$R', —$CF_3$ —NR'$_2$, —NHR', and —$NH_2$, wherein each R' is the same or different and is optionally substituted alkyl or optionally substituted aryl.

16. The method of claim 15, wherein m is 2.

17. The method of claim 15, wherein a portion of the metal ions are associated with four ligands, and each of those ligand is individually associated with two metal ions.

18. The method of claim 15, wherein each ligand comprises two pyrazolates.

19. The method of claim 15, wherein each metal ion is selected from the group consisting of $Mg^{2+}$, $Mn^{2+}$, $Fe^{2+}$, $Co^{2+}$, $Ni^{2+}$, $Cu^{2+}$, $Pd^{2+}$, $Pt^{2+}$, $Ru^{2+}$, $Cd^{2+}$, $Zn^{2+}$, $Pb^{2+}$, $Hg^{2+}$, $V^{2+}$, $Cr^{2+}$, and $Ni^{+2}$.

20. The method of claim 15, wherein each metal ion is $Zn^{2+}$.

21. The method of claim 15, wherein the ligand comprises the structure:

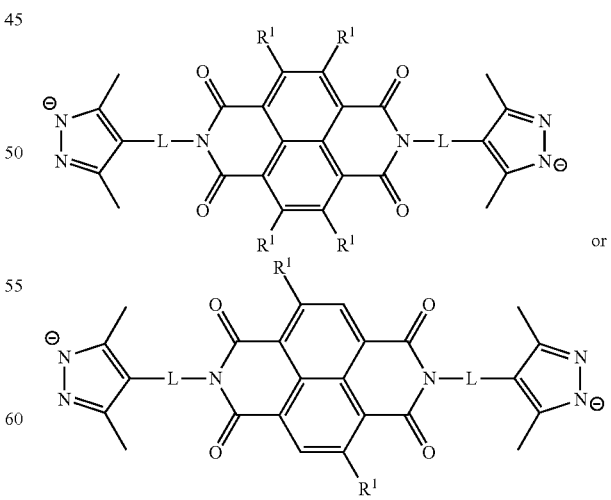

wherein:
  each $R^1$ is the same or different and is selected from the group consisting of hydrogen, —$NO_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$;

each L is the same or different and is absent or selected from the group consisting of optionally substituted alkylene, optionally substituted heteroalkylene, optionally substituted arylene, and optionally substituted heteroarylene; and each R' is the same or different and is optionally substituted alkyl or optionally substituted aryl.

22. The method of claim 15, wherein the ligand comprises the structure:

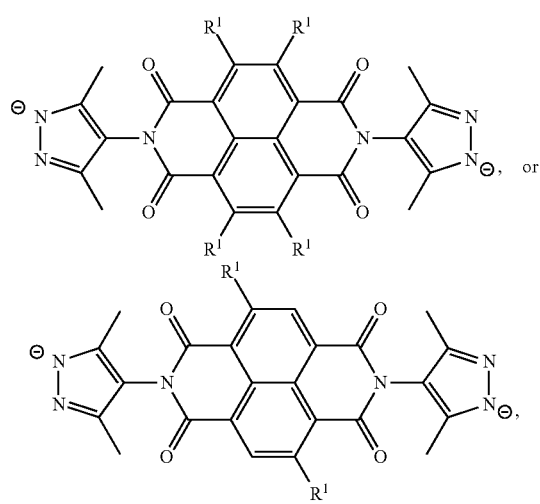

wherein:
each R$^1$ is the same or different and is selected from the group consisting of hydrogen, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$; and each R' is the same or different and is optionally substituted alkyl or optionally substituted aryl.

23. The method of claim 15, wherein the water uptake of the MOF at a relative humidity of approximately 40% is between about 0.2 and about 2 g of water per gram of MOF.

24. A metal organic framework (MOF) comprising:
a plurality of metal ions, each coordinated with at least one ligand, wherein each ligand has the structure [Q-(Ar)$_m$]$^{m-}$, wherein:

each Ar is the same or different and is an unsaturated N-heterocyclic aromatic group selected from the group consisting of pyrazolate, triazolate, imidazolate, and tetrazolate;

m is 2; and

Q comprises the structure:

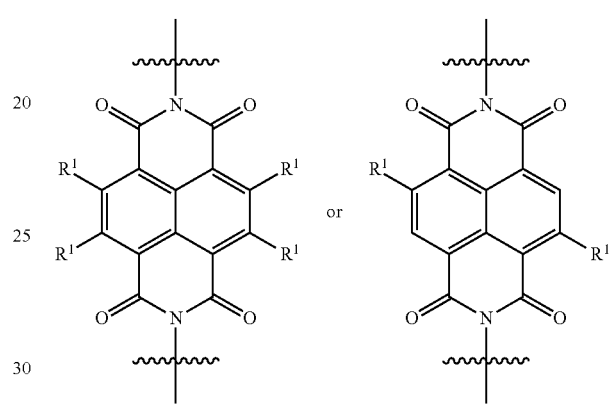

wherein each R$^1$ is the same or different and is selected from the group consisting of hydrogen, —NO$_2$, —R', —F, —Cl, —Br, —I, —CN, —NC, —SO$_3$R', —SO$_3$H, —OR', —OH, —SR', —SH, —PO$_3$R', —PO$_3$H, —CF$_3$, —NR'$_2$, —NHR', and —NH$_2$, wherein each R' is the same or different and is optionally substituted alkyl or optionally substituted aryl.

25. The MOF of claim 2, wherein each Ar is triazolate.

* * * * *